United States Patent [19]

Hannan

[11] Patent Number: 5,175,091
[45] Date of Patent: Dec. 29, 1992

[54] METHOD FOR TOXIN DETECTION

[75] Inventor: Patrick J. Hannan, Bethesda, Md.

[73] Assignee: The United States of America as represented by the Secretary of the Navy, Washington, D.C.

[21] Appl. No.: 102,509

[22] Filed: Sep. 29, 1987

[51] Int. Cl.$^5$ ............................................. C12Q 1/02
[52] U.S. Cl. ........................................ 435/29; 435/4; 435/313; 435/807; 435/818
[58] Field of Search ...................... 435/4.29, 132, 171, 435/255, 284, 291, 296, 313, 807, 818, 942; 436/63, 68, 43

[56] References Cited

U.S. PATENT DOCUMENTS 3,926,737 12/1975 Wilson et al. ...................... 435/289

OTHER PUBLICATIONS

*Microbiology* (3rd ed.), Harper & Row, Hagerstown, pp. 34-35.
"The Detection of Toxins by a New Method Based on the $CO_2$ Production by Yeast", Patrick J. Hannan et al., NRL Memorandum Report 5864, Sep. 30, 1986.

*Primary Examiner*—Sam Rosen
*Attorney, Agent, or Firm*—Thomas E. McDonnell; Barry A. Edelberg

[57] ABSTRACT

A method and apparatus for detecting a toxin whereby a yeast culture is monitored for the release rate of one or more metabolic products before and after the inclusion of a test sample and a decrease in the release rate of the metabolic products indicates the presence of a toxin on the test sample. The method contemplates the use of carbon dioxide-free air as a scrubbing gas to remove carbon dioxide from the media for testing.

9 Claims, 3 Drawing Sheets

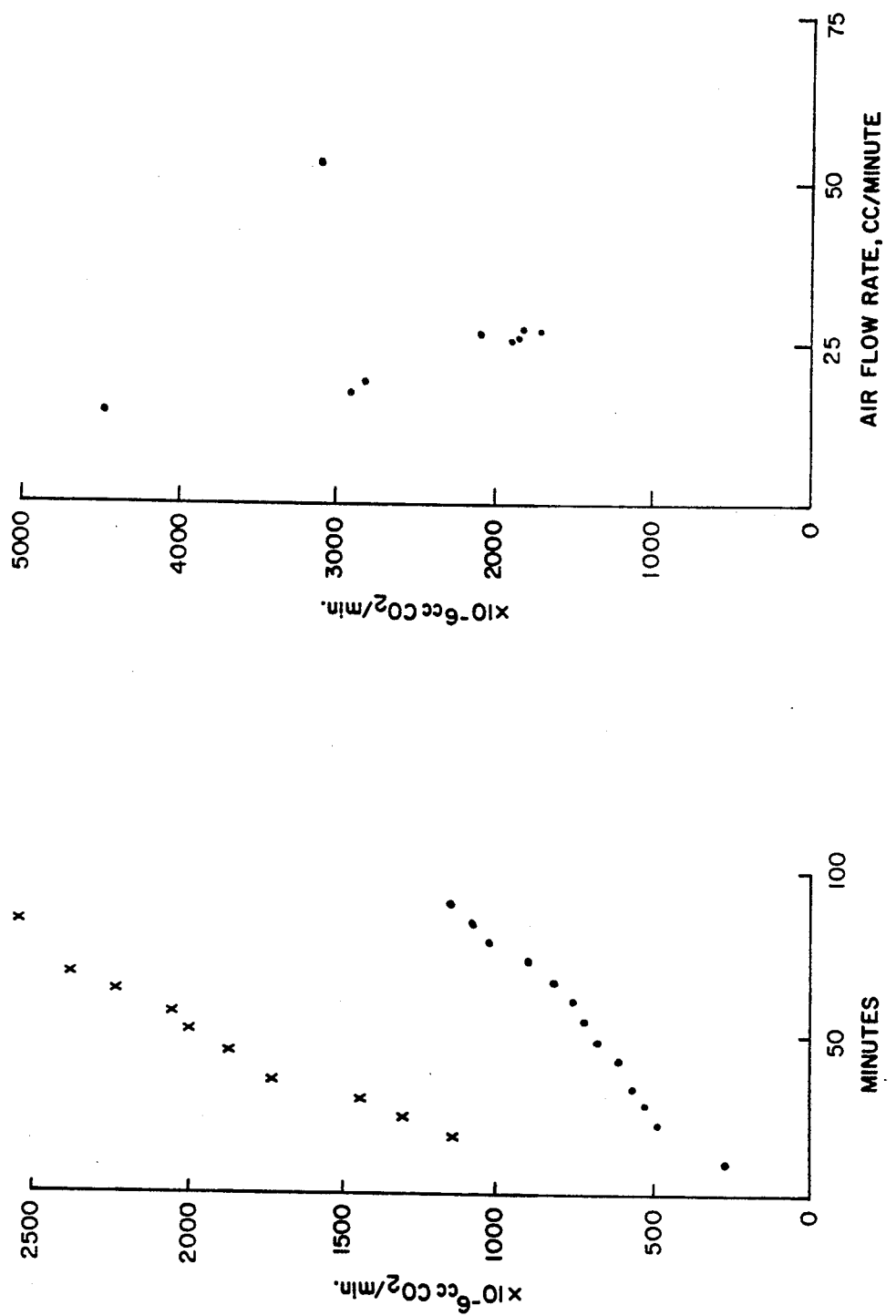

METHOD FOR TOXIN DETECTION

BACKGROUND OF THE INVENTION

The invention pertains generally to toxin detectors and more particularly to portable, field-usable toxin detectors.

A great need exists for the detection and identification of toxins in the field. The seriousness of this need is demonstrated by the controversy over the use of Yellow Rain (trichothecenes) in Southeast Asia and Afghanistan. Allegations by the United States that toxins had been used were disputed when scientists from other countries were unable to detect them in soil and vegetation samples. A major factor in the lack of confirmation was later determined to be the rapid reaction of trichothecenes with vegetation. Other examples of the need for a toxin field detector are grain storage and pollution control.

The detection of toxins can be done by chemical, mechanical or biological procedures, but absolute identifications, at the present time, are by chemical means. For trichothecenes (Yellow Rain compounds), the biological tests include those for lethality in mice and rats, and for dermatitic responses in rats, guinea pigs, and rabbits. A highly specific bioassay for trichothecenes based on $^{14}C$ labelled leucine uptake in rabbit reticulocyte cells has been developed. Fungi have been used as assay organisms. Another test is based on the inhibition of the germination of peas. All of these assays require exposure times of a day or more and employ organisms or animals which are not readily available for field use. One possibility for a more rapid and specific identification of toxins concerns antibody formation; however, effectiveness is limited to only a few trichothecenes. The preferred method for instrumental analysis is gas chromatography/mass spectrometry (GC/MS) but the equipment required is not portable and the interferences posed by contamination of samples with vegetation or other components associated with field samples are substantial.

Presently, no method or apparatus exists that is simple, rugged and inexpensive; can give rapid results with minimal workup; and is reliable outside the laboratory.

SUMMARY OF THE INVENTION

It is, therefore, an object of the present invention to detect toxins without measuring changes in the number of cells or some component of them over a period of time.

Another object of the invention is to detect toxins without killing laboratory animals.

Another object of the invention is to test toxins rapidly, inexpensively, and in the field.

These and other objects are achieved by comparing the rate of release of metabolic products by a yeast culture before and after the introduction of a test sample to determine whether the test sample had an inhibitory effect on the growth of the yeast, an inhibitory effect being an indication of the presence of a toxin.

BRIEF DESCRIPTION OF THE FIGURES

FIG. 3 is graph of the rate of $CO_2$ production as a function of time for two identical cultures with different flow rates.

FIG. 4 is graph of the $CO_2$ release as a function of air flow.

DETAILED DESCRIPTION OF THE INVENTION

Figure 1:
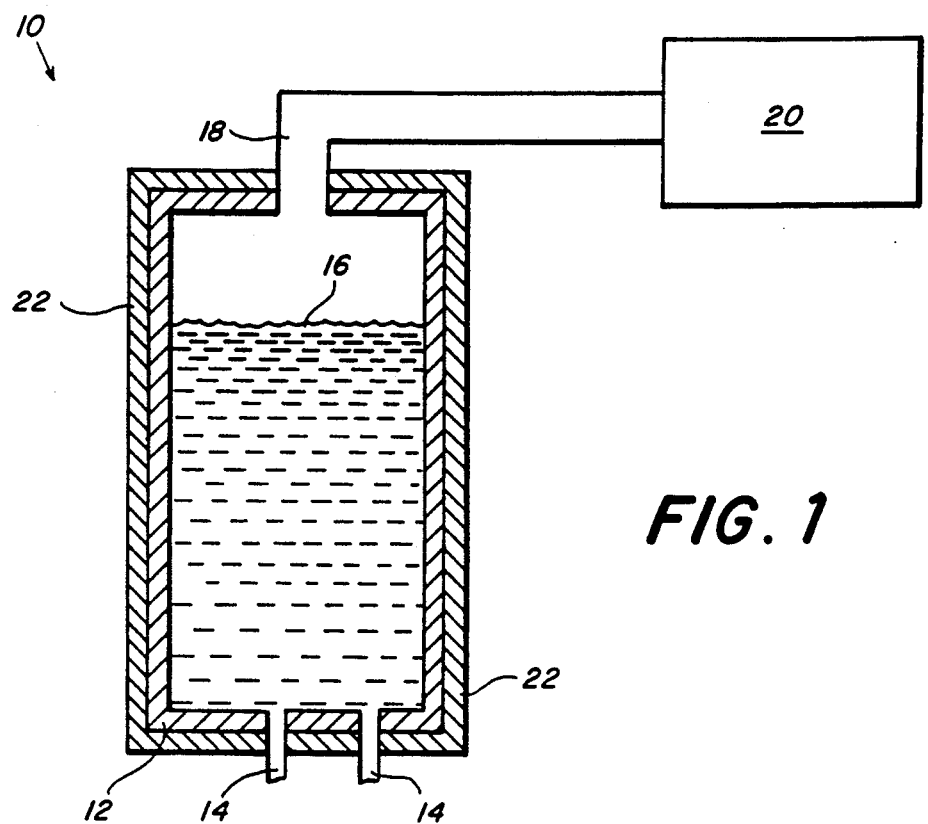
FIG. 1 is a cross sectional view of a single-cavity detector with a plurality of inlet ports.
Figure 2:
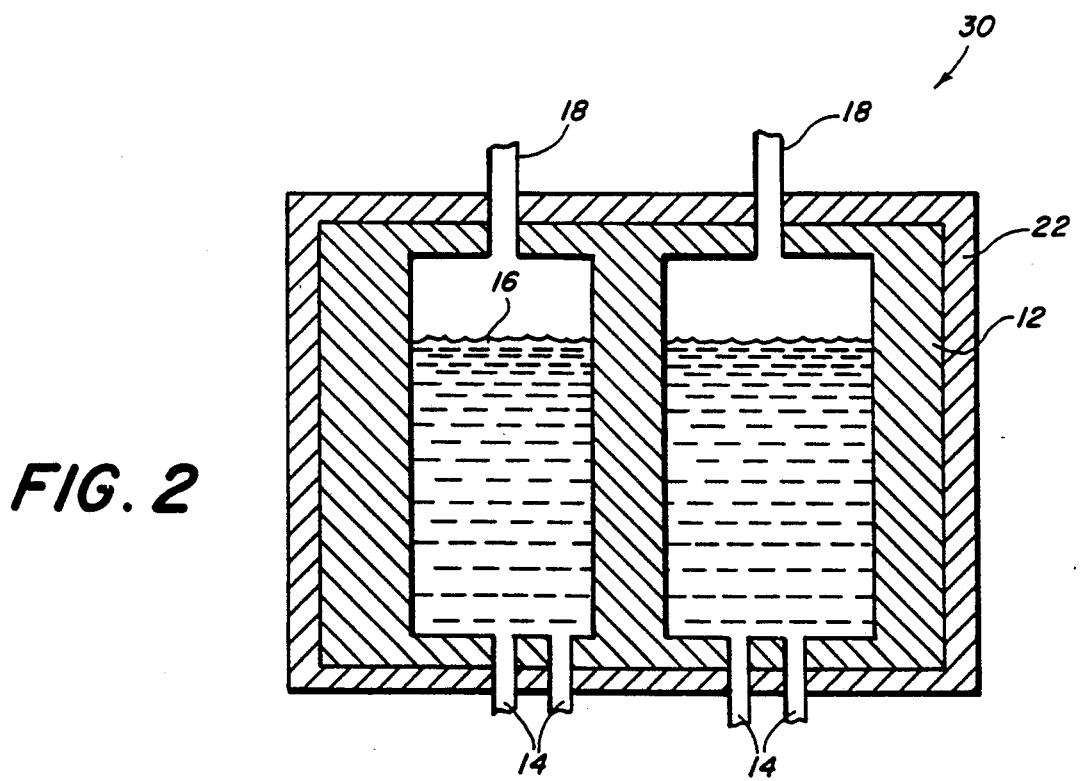
FIG. 2 is a cross sectional view of a double-cavity test chamber with a plurality of inlet ports per cavity.

In FIGS. 1 and 2, like numerals refer to like parts. FIG. 1 is a cross-section view of one embodiment of the toxin detector 10 of this invention, which comprises a test chamber 12 connected to an analyser 20. Test chamber 12 has a single cavity having one or more inlet ports 14 for admitting a carrier gas from a source not shown into a fluid yeast culture 16 in the cavity of test chamber 12. The carrier gas passes through the yeast culture and exits through outlet port 18 to analyser 20. Associated with the detector is a means 22 for maintaining a constant temperature in the yeast culture 16.

The test chamber 30 in FIG. 2 has at least two cavities having one or more inlet ports 14 for admitting a carrier gas that is identical for each cavity into an identical fluid yeast culture 16. The carrier gas passes through each yeast culture and exits through each outlet port 18 to an analyzer (now shown). The temperature of the yeast culture is kept constant by the associated means 22.

The construction of the test chamber is generally not critical. The construction material of the test chamber should be nonabsorptive in order to prevent pollution of subsequent samples. The inlet ports are sized to produce the following bubbles and gas flow rates. The outlet port is large enough to permit an easy removal of the gases exiting the yeast culture. The means used to maintain a constant temperature can be insulation for fast tests, can be a heat wrap, i.e., a wrap with heating coils, a constant-temperature bath or a heated chamber in which the detector is placed. The temperature that has to be maintained is from about 26° C. to about 36° C. and preferably from 30° to 35° C.

The operative mechanism is a sufficient, constant and uniform contact between the carrier gas and the yeast medium that allows one or more metabolic products to be released from the culture and be removed. Accordingly, it is anticipated that a long and narrow tube with a film of the yeast culture on the inside wall of the tube would be effective in the detection of toxins.

A reliable indication of the inhibitory effect of a toxin on the rate of production of one or more metabolic products of a yeast culture is difficult for several reasons. Factors affecting the yeast metabolism must be reduced to one, i.e., the toxin. Not all toxins affect yeast in the same manner. It has been discovered that the choice of the carbohydrate carbon source affects the detection of toxins. The rate and uniformity of the carrier gas passing through the yeast medium greatly affects the release of metabolic products from the yeast medium. If the above variables are kept within the following ranges, a reliable portable detector is provided.

The yeast culture comprises a fermentative yeast, a yeast extract or autolysate, a carbohydrate carbon source, and water. The preferred fermentative yeasts are *Saccharomyces cerevisiae*, and *Kluyveromyces, fragilis*. The preferred carbohydrates are glucose, sucrose, maltose, raffinose, galactose, glycerine and mixtures thereof and the most preferred are sucrose, glucose and mixtures thereof. The water is distilled water. Yeast extract or autolysate is readily available commercially.

The optimum amounts of the ingredients are determined especially for each toxin, yeast and sampling rate, i.e., the flow rate of carrier gas through the yeast culture. The ingredients are added within the following ranges. Broadly, the yeast is from about 0.005 to about 0.05 percent of the total culture weight and preferably from 0.02 to 0.04 weight percent of the culture. The yeast extract is from about 0.05 to about 1.5 percent of total yeast culture weight and preferably from 0.2 to 1.25 weight percent. The carbohydrate carbon source is added in an amount from about 1 to about 3 percent and preferably from 1.5 to 2.5 percent of total medium weight. In addition to the concentrations of the yeast, yeast extract, and carbohydrate carbon source, the relative amounts of each is important. The carbohydrate-yeast extract weight ratio is from about 2:1 to about 20.1 and preferably from 2:1 to 7.5:1. The yeast extract-to-yeast ratio is from about 10:1 to about 30:1 and preferably 15:1. Preferably, the ingredients are at least of the chemically pure grade. The remainder of the culture is water and preferably distilled water.

The gas used to carry the metabolic products from the yeast culture to an analyzer must be non-toxic to yeast and have a constant composition. The preferred carrier gas is air or nitrogen and most preferably the air is carbon dioxide-free.

The rate and the uniformity of the carrier-gas passage are critical to the operation of the subject detector. Preferably the carrier gas is bubbled through the fluid yeast medium at a fixed rate and with equal-size bubbles. The gas bubbles have a diameter from about 0.5 to about 5 percent of that of the yeast culture. Diameter is used in the sense of the dimension of a cross-section that is substantially uniform. Functionally, the rate is high enough to provide an adequate scrubbing of the culture, but not so high as to produce a too diluted sample. Accordingly, the rate of air passage is from about 3,000 to about 10,000 percent per minute of the total volume of the medium. The preferred rate is from 5,000 to 10,000 volume percent per minute.

Having described the invention in general, the following examples are given by way of illustration. It is understood that these examples do not limit this disclosure or the claims to follow in any manner.

The *Saccharomyces Cerevisiae* Examples

1. The Yeast

*Saccharomyces cerevisiae* was obtained commercially under the brand names of Fleishmann's Yeast and Red Star Yeast. A package of the yeast was opened and divided into two lots, one being kept in a refrigerator and the other at room temperature. Each was periodically tested for quality.

2. Yeast Medium

The yeast was added to a medium to produce the culture. The medium comprised:

| Yeast extract | 10 cc of a aqueous 4% stock solution |
|---|---|
| Carbohydrate carbon source | 4 grams |
| Distilled water | 190 cc |

The yeast extract was obtained from Difco Laboratories, and the carbohydrate carbon source used in most studies was sugar (sucrose) purchased commercially. Additional carbohydrates were obtained from Calbiochem-Behring in Los Angeles, Calif.

3. The Test Chamber

Test chambers were constructed in several different ways. The first was a filtering tube containing a fritted glass disc in the middle; the lower portion was necked down to accommodate a rubber tube through which the input air was led to the fritted disc which supported 3 ml of yeast suspension, and the upper portion was closed with a stopper fitted with a glass tube to lead the exit air to the $CO_2$ analyzer The random bubble sizes produced by the glass frits gave unequal $CO_2$ scrubbing rates among the various units, resulting in an unsatisfactory replication of results. An improvement consisted in placing glass beads on each fritted disc, which tended to provide a more uniform interstitial separation than the pores of the frits but placement of the beads was critical. Syringe needles were found to provide more uniform bubble distribution so the second type of culture apparatus was a 5 ml plastic syringe in which the position of the needle was reversed, with the tip extending just inside the base. The culture volume varied from 1 to 3 cc. The third type of apparatus was a block of Teflon bored to provide four columns 10 mm in diameter and 62 mm deep; at the base of each was a horizontal threaded plug through which a syringe needle could be inserted. Culture volumes ranged from 0.8 to 2.5 ml. At the top of either the syringes or the Teflon columns were rubber stoppers with glass tubing to conduct the exit air to the $CO_2$ analyzer. The final, and most satisfactory type, was a glass test tube 18×184 mm fitted with a rubber stopper containing inlet and outlet tubes. Bubbling was provided by a glass tube constructed from a Pasteur pipette.

4. Carrier Gas

Air from the laboratory's compressed air line was stripped of $CO_2$ by passage through a pipe packed with ascarite, a product consisting of a mixture of KOH with a non-fibrous silicate carrier. The outlet of this $CO_2$ scrubber led to a small pipe manifold containing stainless steel needle valves to control the air flow to the test cultures. In anticipation of the use of this assay procedure in the field, a Dual Mode Low Flow Air Sampler (Gilian Instrument Corp., Wayne, N.J.) with a sorbent tube containing ascarite was also used as a source of air.

Air flow rates through each test chamber were determined with a flowmeter (Ace Scientific) which was connected to the outlet of the $CO_2$ analyzer. The calibration of this flowmeter was checked with an independent method and found to be accurate. Air flow rates ranging from 9- to 60-cc/minute were used but most experiments were performed with air flows of 27-29 cc/minute. Nitrogen gas, from a cylinder, was also used successfully as a carrier gas. With nitrogen aeration, the oxygen necessary for $CO_2$ production is derived from preformed sterols and organic acids in the body of the yeast.

5. $CO_2$ Analyzer

The $CO_2$ analyses were performed with a Beckman Model 864 Infrared Analyzer. The most sensitive setting with this instrument is normally 0–500 ppm $CO_2$ but full scale readings of just 100 ppm could be achieved with a simple procedure. Most $CO_2$ measurements were made with the instrument set to read 250 ppm full scale. To do this, the intermediate setting was used initially, and the span adjusted so that a given concentration of $CO_2$ gave a reading equivalent to double that amount, following which the instrument was switched back to the most sensitive scale. Standard gases supplied by Air Products Corp. were used to check the accuracy of this procedure and the agreement was within 5%. Such a discrepancy was not considered serious because the principal object was to determine differences between the $CO_2$ concentrations of a control culture vs one treated with a toxin. Thus, absolute $CO_2$ concentrations were considered less important.

It is customary to use air flow rates of 100 cc/minute, or more, with such a $CO_2$ analyzer but it was found that the analyzer worked well at the flow rates used in these studies. The key was to provide a constant flow of air through the instrument, at all times, at the flow rate to be used during the experiment. The instrument must be "zeroed" and "spanned" at this same flow rate.

6. Toxins

All toxins were made into stock solutions containing 1 microgram/microliter with methanol as the solvent except for the snake venoms which were dissolved in distilled water. Most tests were performed with 5- and 10-microliters of toxin solutions added to the yeast.

7. Procedure

The culture medium was placed in a 250 cc graduated cylinder in the constant temperature bath (35° C.) and aerated with $CO_2$-free air for approximately 30 minutes to remove the dissolved $CO_2$. A prescribed portion was then transferred to a smaller graduated cylinder in which had been placed a weighed amount of yeast and the resulting suspension was stirred magnetically while aeration with $CO_2$-free air was continued. Volumes of cultures used ranged from 0.8 cc to 3.0 cc, and weights of yeast varied from 0.10 mg to 0.50 mg.

Generally there were three cultures in each experiment, one being a control and the others containing toxins at 0.01 to 10-micrograms. Aeration through each was constant with bubbling being provided through #20 gauge needles at 27 cc/minute, or from Pasteur pipettes at 180 cc/minute.

Tubing leading from the cultures was connected sequentially to the $CO_2$ analyzer every three or four minutes; since the incoming air had been stripped of all $CO_2$ it was necessary to measure only the $CO_2$ content of the exit air, and the $CO_2$ production was calculated as follows:

$$CO_2 \text{ production rate} = \frac{\text{air flow rate (cc/minute)} \times \text{ppm } CO_2 \text{ in exit air}}{10^6}$$

Because of the permeability of gum rubber tubing to $CO_2$, the rubber connectors in the assembly were kept to a minimum. For field use it would be advantageous to use less permeable tubing, such as, polyethylene or glass.

Table I summarizes the effect of the carbohydrate carbon source had on the release of carbon dioxide. The culture cavities were 5 ml syringes.

TABLE 1

| Carbohydrate | cc $CO_2$/Minute $\times 10^{-6}$ |
|---|---|
| \multicolumn{2}{l}{$CO_2$ Release Rate of .25 mg Yeast (Ater 30 Minutes Incubation) As a Function of the Carbohydrate Used} |
| Mannitol | 0 " |
| Glycerine | 140 " |
| Galactose | 180 " |
| Raffinose | 200 " |
| Maltose | 230 " |
| Sucrose | 635 " |
| Glucose | 760 " |

As was stated before, bubble size and uniformity are critical to the operation of the present detector. Experiments with different constructions for the test chamber demonstrated this importance. The bubble distribution given by glass frits was not sufficiently uniform to give good replication of results. A further insight into the problem was gained from an experiment in which aliquots of a suspension were placed in test chambers having a glass frit in the middle; in one case air was passed through the frit but, in the other, air was passed through a fine needle extending into the suspension, and the frit was blocked by a layer of aluminum foil. The fine bubbles provided by the needle stripped out the $CO_2$ much more rapidly than those from the frit.

FIG. 3 demonstrates the above conclusion by comparing the $CO_2$-release rates of identical yeast cultures of 0.25 mg of yeast in 3 ml medium with sucrose that was aerated with a No. 26 gauge needle at a flow rate of 27 cc/min. The data points marked with "x" are from the "needle" aeration and the ones marked with "." are from the "frit" aeration. Aside from the obvious advantage in using the fine bubbles, the experiment also demonstrated that the productivity of the culture should be considered in terms of a "$CO_2$ release rate" instead of a "$CO_2$ production rate".

It had been assumed that the $CO_2$ release rate from a yeast suspension would increase with air flow rate until a point where the release rate was equal to the production rate. A lengthy series of experiments showed that this was not necessarily the case. With the Teflon culture apparatus used in these studies the weight of yeast was 0.25 mg, the culture volume was 1.0 ml, sucrose was the carbohydrate, and #20 gauge syringe needles were used as bubblers. Difficulties in establishing air flow rates between 29- and 44-cc/minute made it impossible to include that region in these studies, and constant monitoring was needed to include flow rates around 60 cc/minute.

The data representing the $CO_2$ release rates at the 30-minute mark are summarized in FIG. 4 for suspension of 0.5 mg yeast is 1.0 ml medium and they show a definite minimum $CO_2$ release rate at at approximately 29 cc/minute. Observations of the bubbling pattern indicated that at air flow rates below 20 cc/minute the ebullition of bubbles was uniform and the total volume of culture remained at the bottom of the column in the Teflon apparatus. However, at flow rates between 20- and 29-cc/minute, there was considerable spattering of the culture along the walls, leaving discrete droplets which were not subjected to the same efficient $CO_2$ scrubbing one would get with a fine bubble rising through the suspension. Above 29 cc/minute there evidently was an intermediate situation (perhaps fluidization) in which bubble passage was again a factor although this is conjecture. With the 18×18 mm test tubes, there was no problem, and the rate of $CO_2$ release increased with no increase of carrier gas flow rate, up to a maximum. The point to be emphasized is that comparisons between controls and toxin treated cultures are valid only if the air flow rates and the bubble distribution through them are the same.

Figure 5:
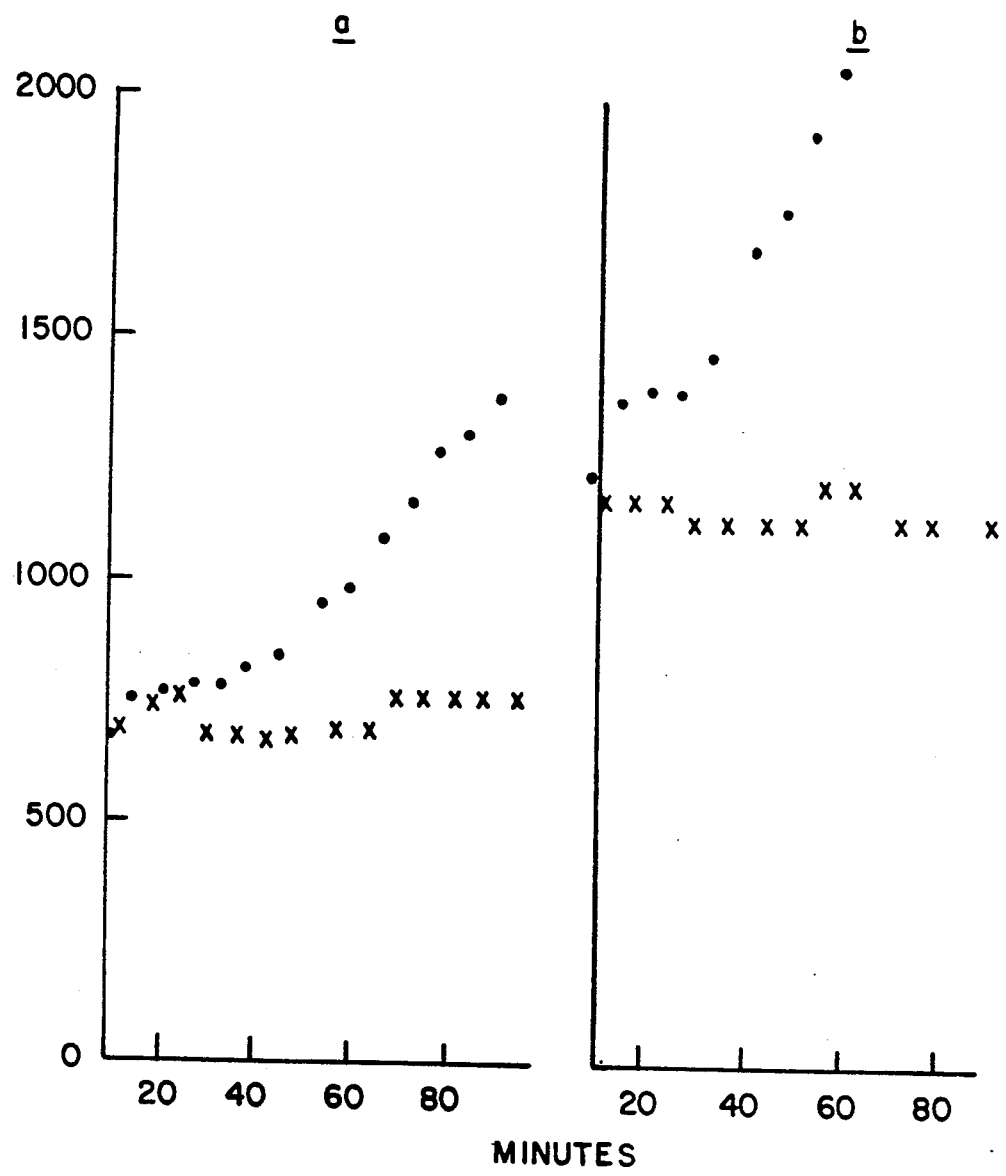
FIGS. 5a and b are graphs of $CO_2$ production as a function of time at different air flow rates.

Since speed would be important in the performance of a detector in the field, it was important to learn the set of conditions which would provide the most rapid indication of a toxin's presence The effect of air flow rate was coupled with the weight of yeast as a variable in two experiments involving 2 micrograms of verrucarin as the toxin. The intent was to determine the $CO_2$ release rate with one combination of yeast weight and air flow rate (0.25 mg in 3 ml and 27 cc/minute) and then double both of those values. Under such conditions the range of $CO_2$ concentrations in the air stream would be approximately the same. The culture chambers were 5 cc syringes and the volume of suspension in each was 3 cc. The desired air flow rate in the second experiment, 54 cc/minute, was unobtainable and 46 cc/minute was used in its stead. The results in FIGS. 5a and b wherein "." represent the control sample and "x" represents the culture sample demonstrate the merit of the faster flow rate for the rapid detection of the toxin. With the higher air flow rate, the toxic effect was evident at 12 minutes, compared with 30 minutes at the lower air flow rate.

Table II summarizes the detectable limits of several toxins tested by the above method.

TABLE II

| Toxin | Detectable Limit |
|---|---|
| verrucarin A | 2 μg |
| T-2 | 3 μg |
| roridin A | 2 μg |
| diacetoxyscirpenol | 5 μg |
| patulin | 10 μg |
| rubratoxin B | 5 μg |
| ochratoxin | 10 μg |
| PR toxin | 5 μg |
| aflatoxin $B_1$ | 710 μg |
| baccharin | 710 μg |
| penicillic acid | 710 μg |

The *Klugveromyces fragilis* Examples

The aforedescribed procedure was repeated for *Kluyveromyces fragilis*. Table III summarizes the detectable limits of various toxins.

TABLE III

| Toxin | Detectable Limit |
|---|---|
| verrucarin A | .03 μg |
| T-2 | 0.2 μg |
| roridin A | 0.12 μg |
| diacetoxyscirpenol | 3.0 μg |

Additional discussion of the results of the above examples is given in Patrick J. Hannan and Sekethia L. Smith "The Detection of Toxin by a New Method Based on $CO_2$ Production by Yeast" NRL Memorandum Report No. 5864, Sep. 30, 1986, which is hereby incorporated by reference. One major advantage of the present method and apparatus is the speed in demonstrating the inhibitory effect of a toxin. In a matter of minutes, a determination can be made by this method and apparatus.

Other important advantages are the simplicity and smallness of the apparatus, allowing the invention to be practiced anywhere.

Obviously many modifications and variations of the present invention are possible in light of the above teachings. It is therfore to be understood that within the scope of the appended claims, the invention may be practiced otherwise than as specifically described.

What is claimed and desired to be secured by Letters Patent of the United States is:

1. A method for detecting a toxin that comprises:
   providing a first and second identical fluid fermentative yeast culture comprising a yeast, a yeast extract, a carbohydrate carbon source and water;
   bubbling carbon dioxide-free air with a known identical and constant composition as a carrier gas though each of said yeast cultures, in at least one stream of bubbles for each yeast culture, at an identical constant rate and in an identical uniform manner at a constant temperature from about 26° to about 36° C., said bubbles having a substantially uniform diameter from about 0.5 to about 5 percent of the diameter of said yeast culture;
   monitoring said carrier gas after exiting from each of said yeast cultures for the rate of release of carbon dioxide from said yeast cultures, said rate of release being substantially equal for both yeast cultures;
   adding a test sample suspected of containing a toxin to said first yeast sample;
   continuing to monitor each carrier gas for the rate of release of said carbon dioxide, a decrease in the release rate for said carbon dioxide form said first yeast culture relative to the release rate for said second yeast culture indicating the presence of said toxin in said yeast sample.

2. The method of claim 1 wherein said fermentative yeast is selected from the group consisting of *Saccharomyces cerevisiae, Kluyveromyces fragilis* and mixture thereof.

3. The method of claim 1 wherein said yeast culture comprises, based on total culture weight, from about 0.005 to about 0.05 weight percent of *Saccharomyces cerevisiae*; from about 0.05 to about 1.5 weight percent of a yeast extract; from about 1 to about 3 weight percent of a carbohydrate carbon source selected from the group consisting of glucose, sucrose, maltose, raffinose, galactose, glycerine and mixtures thereof, said carbohydrate carbon source having a weight ratio to said yeast extract from about 2:1 to about 20:1 and said yeast extract-to-yeast weight ratio is from about 10:1 to about 100:1; and water.

4. The method of claim 1 wherein said yeast culture comprises, based on total culture weight, from about 0.005 to about 0.03 weight percent of *Kluyveromyces fragilis*, and from about 0.05 to about 1.5 weight percent of a yeast extract; from about 1 to about 3 weight percent of a carbohydrate carbon source selected from the group consisting of glucose, sucrose, maltose, raffinose, galactose, glycerine and mixture thereof, said carbohydrate carbon source and yeast extract having a carbohydrate-yeast extract weight ratio from about 2:1 to about 20:1 and said yeast extract and said yeast having a extract-to-yeast weight ratio is from about 10:1 to about 30:1.

5. The method of claim 3 wherein said gas is bubbled through said yeast cultures at a rate, based on total volume of one yeast culture, from about 4 volume percent per minute to about 40 volume percent per minute.

6. The method of claim 4 wherein said gas is bubbled through said yeast culture at a rate, based on total volume of one yeast culture from about 3,000 volume percent per minute to about 10,000 volume percent per minute.

7. The method of claim 3 wherein said bubbles of gas have a diameter from 1 to 4 percent of the diameter of the yeast culture and said gas is bubbled through said yeast culture at a rate from 10 to 100 volume percent per minute.

8. The method of claim 7 wherein said yeast culture comprises, based on total culture weight, from 0.02 to 0.04 weight percent of Saccharomyces cerevisiae; from 0.2 to 1.2 weight percent of a yeast extract; from 1.5 to 2.5 weight percent of a carbohydrate carbon source selected from the group consisting of sucrose, glucose and mixtures thereof, said carbohydrate carbon source and yeast extract having a carbohydrate-extract weight ratio from 2:1 to 7.5:1 and said yeast and yeast extract having an extract-yeast weight ratio from 10:1 to 30:1.

9. A method for detecting a toxin that comprises
bubbling at least one stream of carbon dioxide-free air of a known and constant composition as a carrier gas though a fluid yeast culture comprising a yeast, a yeast extract, a carbohydrate carbon source and water, at a constant rate and in a uniform manner at a constant temperature from about 26° to about 36° C., said bubbles having a substantially uniform diameter from about 0.5 to about 5 percent of the diameter of said yeast culture;

monitoring said gas after exiting said yeast medium for the rate of release of carbon dioxide to establish a base rate;

adding a test sample suspected of containing a toxin to said yeast medium; and continuing to monitor said gas for a change in the release rate of said carbon dioxide, said change indicating the presence of said toxin on or in said test sample.

* * * * *